US010602993B2

(12) United States Patent
Guo (10) Patent No.: US 10,602,993 B2
(45) Date of Patent: Mar. 31, 2020

(54) IMAGE RECONSTRUCTION FOR Z-FLYING FOCAL SPOT TOMOGRAPHY

(71) Applicant: FMI Medical Systems Co., Ltd., Zhejiang (CN)

(72) Inventor: Hongbin Guo, Champaign, IL (US)

(73) Assignee: FMI Medical Systems Co., Ltd., Zhejiang (CN)

(*) Notice: Subject to any disclaimer, the term of this patent is extended or adjusted under 35 U.S.C. 154(b) by 131 days.

(21) Appl. No.: 15/983,500

(22) Filed: May 18, 2018

(65) Prior Publication Data
US 2019/0350539 A1    Nov. 21, 2019

(51) Int. Cl.
*A61B 6/03*        (2006.01)
*H01J 35/14*       (2006.01)
*A61B 6/00*        (2006.01)
*H01J 35/30*       (2006.01)

(52) U.S. Cl.
CPC ............ *A61B 6/032* (2013.01); *A61B 6/4021* (2013.01); *H01J 35/14* (2013.01); *H01J 35/30* (2013.01)

(58) Field of Classification Search
CPC ........ A61B 6/032; A61B 6/4021; H01J 35/30; H01J 35/14
See application file for complete search history.

(56) References Cited

U.S. PATENT DOCUMENTS

| | | | | | |
|---|---|---|---|---|---|
| 5,841,831 | A | * | 11/1998 | Hell | A61B 6/032 378/19 |
| 6,597,756 | B1 | * | 7/2003 | Basu | A61B 6/032 378/15 |
| 7,809,100 | B2 | * | 10/2010 | Shechter | G01T 1/2985 378/4 |
| 8,175,218 | B2 | | 5/2012 | Hein et al. | |
| 2004/0081270 | A1 | * | 4/2004 | Heuscher | A61B 6/032 378/4 |
| 2008/0247504 | A1 | * | 10/2008 | Edic | A61B 6/032 378/9 |

(Continued)

OTHER PUBLICATIONS

Image Reconstruction and Image Quality Evaluation for a 64-Slice CT Scanner with Z-Flying Focal Spot; T.G. Flohr, et al.; Med. Phys. 32 (8), Aug. 2005; pp. 2536-2547.

(Continued)

*Primary Examiner* — Marcus H Taningco
(74) *Attorney, Agent, or Firm* — Fishman Stewart PLLC (57) ABSTRACT

A computed tomography (CT) system includes a rotatable gantry having an opening to receive an object to be scanned, an x-ray tube having an anode, the x-ray tube positioned on the rotatable gantry to generate x-rays from a first focal spot at a first z-location, and from a second focal spot at a second z-location, a pixelated detector positioned on the rotatable gantry to receive the x-rays from the first z-location and from the second z-location, and a computer. The computer is programmed to acquire a first dataset in a fan geometry at a first z-location, acquire a second dataset in the fan geometry at a second z-location, and reconstruct an image based on the first dataset and the second dataset, wherein the reconstruction is performed without combining the first dataset and the second dataset into one dataset with a single geometry from which the image reconstruction is performed.

20 Claims, 8 Drawing Sheets

(56) References Cited

U.S. PATENT DOCUMENTS

| | | | | |
|---|---|---|---|---|
| 2009/0161815 A1* | 6/2009 | Grass | ............ | A61B 6/032 |
| | | | | 378/5 |
| 2009/0168952 A1* | 7/2009 | Mori | ............ | A61B 6/032 |
| | | | | 378/15 |
| 2009/0279659 A1* | 11/2009 | David | ............ | A61B 6/032 |
| | | | | 378/7 |
| 2013/0266115 A1* | 10/2013 | Fan | ............ | A61B 6/06 |
| | | | | 378/16 |
| 2013/0308746 A1* | 11/2013 | Ueki | ............ | A61B 6/032 |
| | | | | 378/9 |

OTHER PUBLICATIONS

Flying Focal Spot (FFS) in Cone-Beam CT; Marc Kachelriell, Member IEEE, Michael Knaup, Christian Perael, and Willi A. Kalender; IEEE Transactions on Nuclear Science, vol. 53, No. 3, Jun. 2006; pp. 1238-1247.

Impact of the Z-Flying Focal Spot on Resolution and Artifact Behavior for a 64-Slice Spiral CT Scanner; Yiannis Kyriakou et al.; Eur Radiol (2006) 16: Dec. 6, 1215; DOI 10.1007/s0 0330-005-0118-9; Computer Tomography.

\* cited by examiner

IMAGE RECONSTRUCTION FOR Z-FLYING FOCAL SPOT TOMOGRAPHY

TECHNICAL FIELD

This disclosure relates generally to diagnostic imaging and, more particularly, to an apparatus and method of reducing artifacts for z-flying focal spot in computed tomography (CT) system.

BACKGROUND

Typically, in computed tomography (CT) imaging systems, a rotatable gantry includes an x-ray tube, detector, data acquisition system (DAS), and other components that rotate about a patient that is positioned at the approximate rotational center of the gantry. X-rays emit from the x-ray tube, are attenuated by the patient, and are received at the detector. The detector typically includes a photodiode-scintillator array of pixelated elements that convert the attenuated x-rays into photons within the scintillator, and then to electrical signals within the photodiode. The electrical signals are digitized and then received within the DAS, processed, and the processed signals are transmitted via a slipring (from the rotational side to the stationary side) to a computer or data processor for image reconstruction, where an image is formed.

The gantry typically includes a pre-patient collimator that defines or shapes the x-ray beam emitted from the x-ray tube. X-rays passing through the patient can cause x-ray scatter to occur, which can cause image artifacts. Thus, x-ray detectors typically include an anti-scatter grid (ASG) for collimating x-rays received at the detector. Imaging data may be obtained using x-rays that are generated at a single polychromatic energy. However, some systems may obtain multi-energy images that provide additional information for generating images.

Third generation multi-slices CT scanners typically include a detector assembly having scintillator/photodiodes arrays positioned in an arc, where the focal spot is the center of the corresponding circle. The material used in these detectors generally has scintillation crystal/photodiode arrays, where the scintillation crystal absorbs x-rays and converts the absorbed energy into visible light. A photodiode is used to convert the light to an electric current. The reading is typically proportional and linear to the total energy absorbed in the scintillator.

In X-ray computed tomography (CT) imaging systems, the x-ray tube generates high speed electrons from the filament. The electrons fly toward the positive target anode, in which the energy of the electrons is converted to X-rays. In conventional CT scanners, the X-ray emits from one focal spot on the anode plate. For multi-row scanners, to increase the resolution and reduce or remove under-sampling related image artifacts the so-called "Flying focal spot" (FFS), i.e. the focal spot is periodically moved among certain given positions, can be employed. The in-plane focal spot motion can increase resolution of transverse planes while the motion in the z-direction, referred to hereinafter as zFFS, which can increase axial resolution.

In a conventional single focal spot cone beam (CB) system, the sampling interval in the z-direction is the same as detector height of each row. The practical detector height is constrained by production technology and cost, and can cause windmill artifacts of helical scans in high contrast regions. zFFS strategy can increase the sampling rate in the z-direction, thus it not only can boost the z-resolution but also reduce helical windmill artifacts. According to this disclosure a fundamental circular cone beam (CCB) scan protocol is used to present the disclosed method, but it is contemplated that the disclosure is applicable to helical scans, as well.

X-ray Tomography is widely used in clinical disease diagnosis. The zFFS strategy has been proposed for several years and CT scanner venders have produced products to implement the focal spot wobbling idea. In general, current image reconstruction methods for zFFS scanning treat detector readings from alternating two focal spots as interleaved sampling, i.e. group the two sets of data to one set by interleaving the rows of each consecutive (odd and even) reading pair to build one sinogram with double number of rows. Then, the combined data is used for image reconstruction by a regular single focal spot geometry, either using a native fan geometry, or by re-binning the data to a parallel geometry. This type of reconstruction method, using combined data, has at least two drawbacks:

1) Small FOV: rebuilding data sets by interleaving assumes that the rays from two focal spots are stacked alternatively in a z-direction, which is true for a limited FOV. This assumption does not hold for the voxels close to focal spots. And, in fact, in one example the assumption only holds for a field-of-view (FOV) of about 200 mm for some known commercial scanners.

2) Inaccuracy: For voxels out of the limited FOV the interleaved data may cause mistakes. And, for voxels within the limited FOV the interleave strategy may also introduce inaccuracy since a geometrically "perfect" and equally spaced z-interleave for the combined data only happens at the z-axis. That is, the further the voxel from the z-axis, the worse the violation of the equal space assumption.

Thus, there is a need to improve zFFS reconstruction algorithms for both CCB and helical scans.

BRIEF DESCRIPTION

The disclosure is directed toward an apparatus, method of fabricating, and method of using a zFFS strategy in computed tomography (CT)

A computed tomography (CT) system includes a rotatable gantry having an opening to receive an object to be scanned, an x-ray tube having an anode, the x-ray tube positioned on the rotatable gantry to generate x-rays from a first focal spot at a first z-location, and from a second focal spot at a second z-location, a pixelated detector positioned on the rotatable gantry to receive the x-rays from the first z-location and from the second z-location, and a computer. The computer is programmed to acquire a first dataset in a fan geometry at a first z-location, acquire a second dataset in the fan geometry at a second z-location, and reconstruct an image based on the first dataset and the second dataset, wherein the reconstruction is performed without combining the first dataset and the second dataset into one dataset with a single geometry from which the image reconstruction is performed.

A method of computed tomography (CT) imaging includes acquiring a first dataset in a fan geometry at a first z-location of an x-ray tube anode, acquiring a second dataset in the fan geometry at a second z-location of the x-ray tube anode, and reconstructing an image based on the first dataset and the second dataset. The reconstruction is performed without combining the first dataset and the second dataset into one dataset with a single geometry from which the image reconstruction is performed.

Various other features and advantages will be made apparent from the following detailed description and the drawings.

DETAILED DESCRIPTION

The operating environment of disclosed examples is described with respect to a multislice computed tomography (CT) system. Examples are described with respect to a "third generation" CT scanner, however it is contemplated that the disclosed examples are applicable to other imaging systems as well, and for CT systems having more or less than the illustrated sixty-four-slice system.

Figure 1:
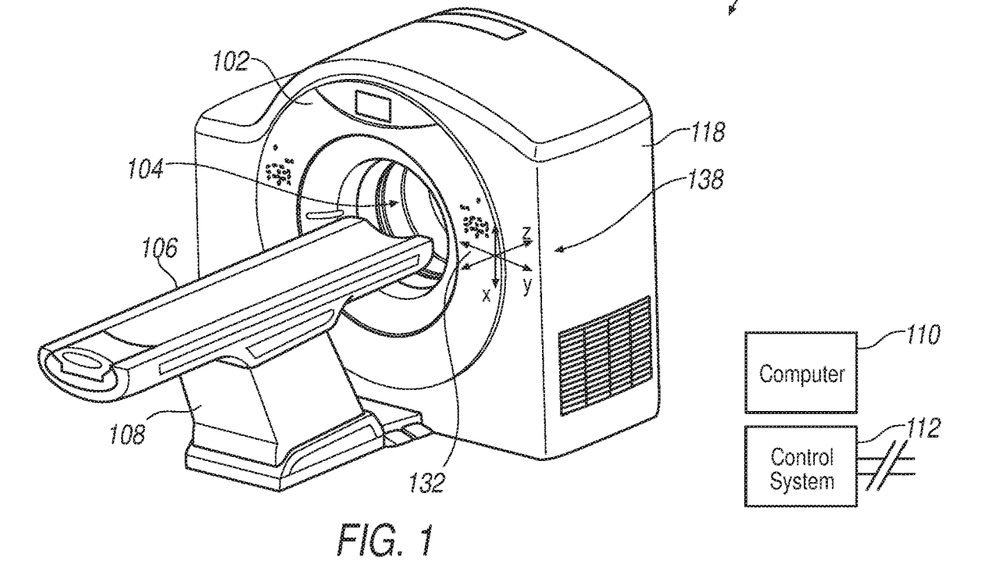
FIG. 1 is a perspective view of a CT imaging system.
Figure 2:
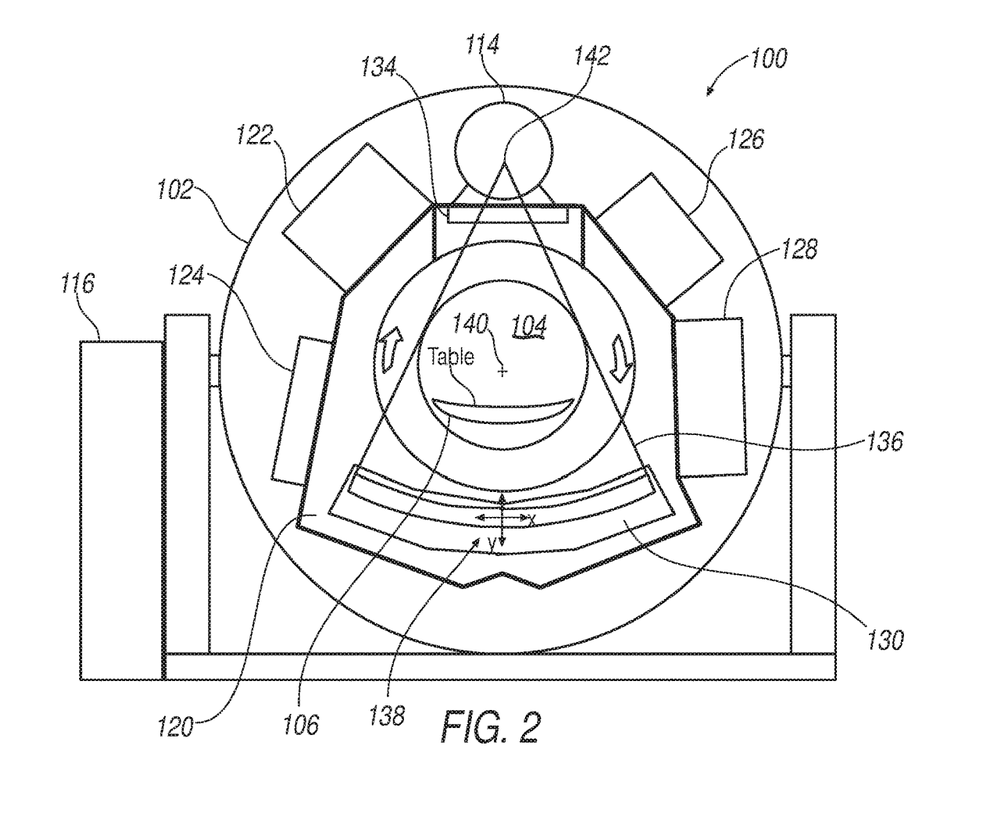
FIG. 2 is a planar cross-section of the system illustrated in FIG. 1.

Referring to FIGS. 1 and 2, a computed tomography (CT) system 100 includes a gantry 102 having an opening 104. A patient table 106 is positioned on a support structure 108, and patient table 106 is axially controllable such that a patient (not shown) positioned on table 106 may be positioned within opening 104. A computer system 110 provides operator instructions and other control instructions to a control system 112. Computer system 110 also may include image reconstruction programs, or an image reconstructor may be provided as a separate processing unit. Control system 112 provides control commands for operating gantry 102, an x-ray tube 114, and a gantry motor controller 116, as examples. Gantry 102 includes a cover or enclosure 118, which provides for aesthetic improvement, safety, etc.

Gantry 102 includes a rotatable base 120, on which is mounted x-ray tube 114, a heat exchanger 122, a data acquisition system (DAS) 124, an inverter 126, a high-voltage generator 128 for generating high voltage in x-ray tube 114, and a detector assembly 130, as examples. System 100 is operated with commands entered by a user into computer 110. Gantry 102 may include gantry controls 132 located thereon, for convenient user operation of some of the commands for system 100. Detector assembly 130 includes a plurality of detector modules (not shown), which include an anti-scatter grid (ASG), scintillators, photodiodes, and the like, which detect x-rays and convert the x-rays to electrical signals, from which imaging data is generated. Gantry 102 includes a pre-patient collimator 134 that is positioned to define or shape an x-ray beam 136 emitted from x-ray tube 114. Although not shown, a shape filter may be positioned for instance between x-ray tube 114 and pre-patient collimator 134.

In operation, rotatable base 120 is rotating about the patient, and table 106 is enabled to move the patient axially into the opening 104. When a desired imaging location of the patient is proximate an axial location where x-ray beam 136 will be caused to emit, x-ray tube 114 is energized and x-ray beam 136 is generated from a focal spot within x-ray tube 114. The detectors receive x-rays, some of which have passed through the patient, yielding analog electrical signals are digitized and passed to DAS 124, and then to computer 110 where the data is further processed to generate an image. The imaging data are stored on computer system 100 and images may be viewed. An X-Y-Z triad 138, corresponding to a local reference frame for components that rotate on rotatable base 120, defines a local directional coordinate system in a gantry circumferential direction X, a gantry radial direction Y, and gantry axial direction Z. Accordingly, and referring to triad 138, the patient passes parallel to the Z-axis, the x-rays pass along the Y axis, and the rotational components (such as detector assembly 130) rotate in a circumferential direction and in the X direction, and about an isocenter 140 (which is a center point about which rotatable base rotates, and is an approximate position of the patient for imaging purposes). A focal spot 142 is illustrated within x-ray tube 114, which corresponds to a spot from which x-ray beam 136 emits.

Figure 3:
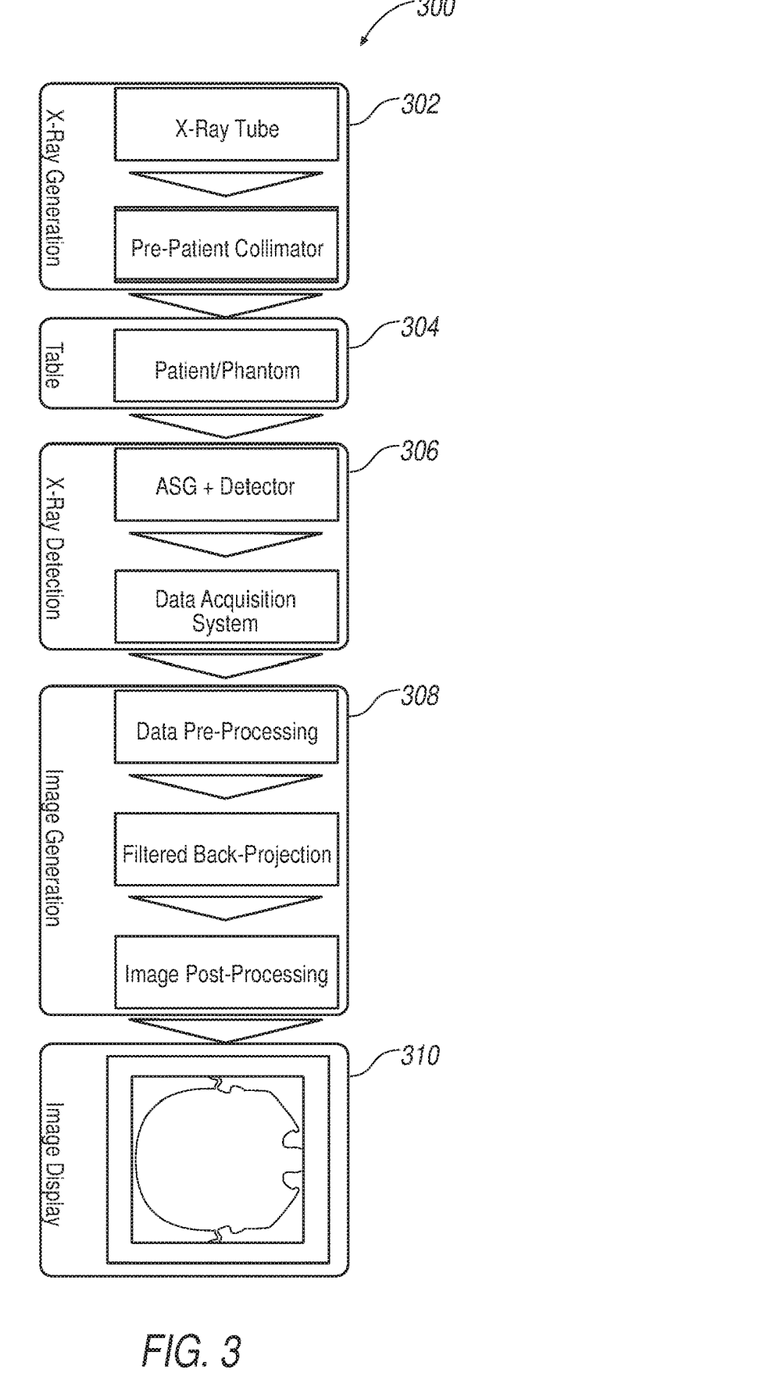
FIG. 3 is an example of an imaging chain.

FIG. 3 illustrates an exemplary image chain 300, consistent with the operation described with respect to FIGS. 1 and 2. X-ray generation 302 occurs, using x-ray tube 114 and passing x-rays through pre-patient collimator 134, during which patient table 106 passes 304 through opening 104 of gantry 102. In one example table 106 may have a patient thereon, and in another example a phantom may be used for calibration purposes.

X-ray detection 306 occurs when x-rays having been emitted from x-ray tube 114 pass to detector assembly 130. An anti-scatter grid (ASG) prevents x-ray scatter (emitting for example from the patient as secondary x-rays and in a direction that is oblique to x-ray beam 136), by generally filtering x-rays that emit from x-ray tube 114. DAS 124 processes signals received from detector assembly 130. Image generation 308 occurs after the digitized signals are passed from a rotating side of gantry 102 (on rotatable base 120) to a stationary side, via for instance a slip-ring.

Image generation 308 occurs in computer system 110, or in a separate processing module that is in communication with computer system 110. The data is pre-processed, and image views or projections are used to reconstruct images using known techniques such as a filtered backprojection (FBP). Image post-processing also occurs, after which the images may be displayed 310, or otherwise made available for display elsewhere (such as in a remote computing device).

Figure 4:
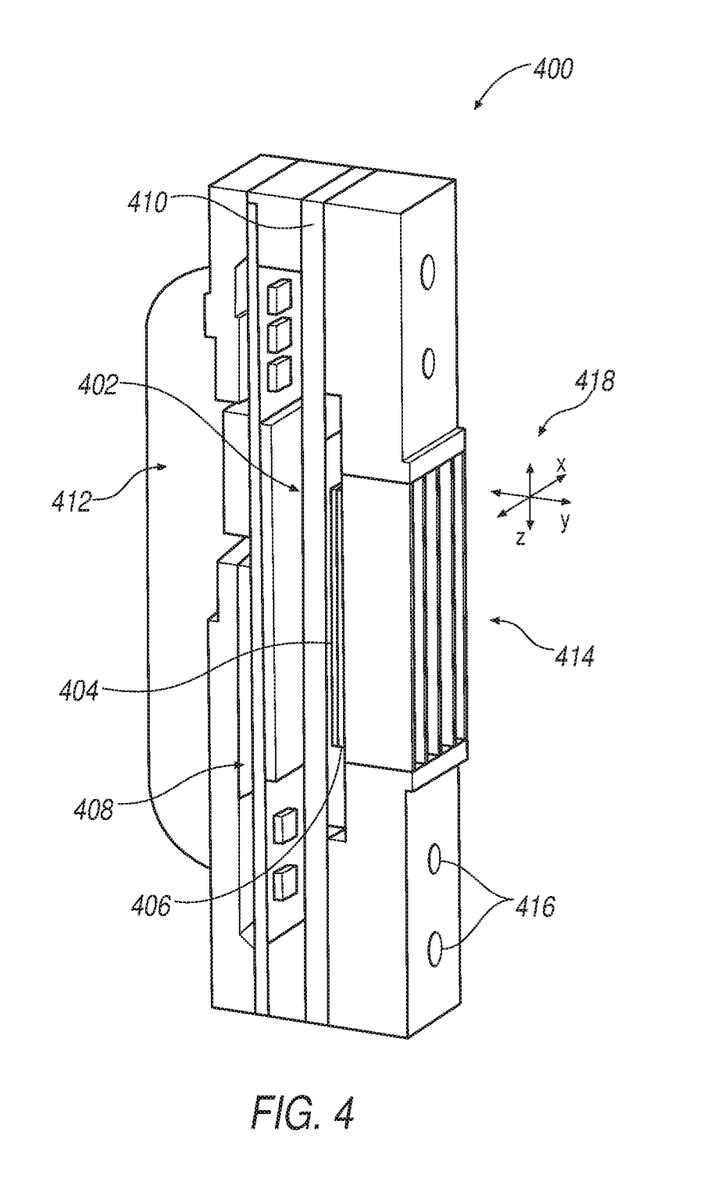
FIG. 4 is an example of a detector module.

FIG. 4 illustrates an exemplary detector module 400 that is one of a plurality of modules for use in detector assembly 130. A diode-scintillator array 402 includes a pixelated scintillator 406 positioned on a pixelated photodiode array 404. The photodiode array 404 may be either a front-lit or a back-lit type of photodiode. The diode-scintillator array 402 is positioned on an A/D board 408 that includes electronics components for signal processing, wherein analog electrical signals from diode-scintillator array 402 are digitized and then passed to DAS 124. Diode-scintillator array 402 is positioned on a base substrate 410 that may include a ceramic or other solid base material. A heat sink 412 is in thermal contact with A/D board 408 for providing enhanced cooling to the electronics located on A/D board 408. Detector module 400 also includes an anti-scatter grid (ASG) 414 that, in one embodiment, includes a plurality of plates (a few exemplary plates are shown) that are approximately parallel with a Y-Z plane of detector assembly 130. ASG 414, in the illustrated example, includes mount holes 416 which may be used for mounting module 400 to detector assembly 130 and aligning it therewith. FIG. 4 illustrates a triad 418 that illustrates corresponding X-Y-Z coordinates, as illustrated also in FIG. 1.

Figure 5:
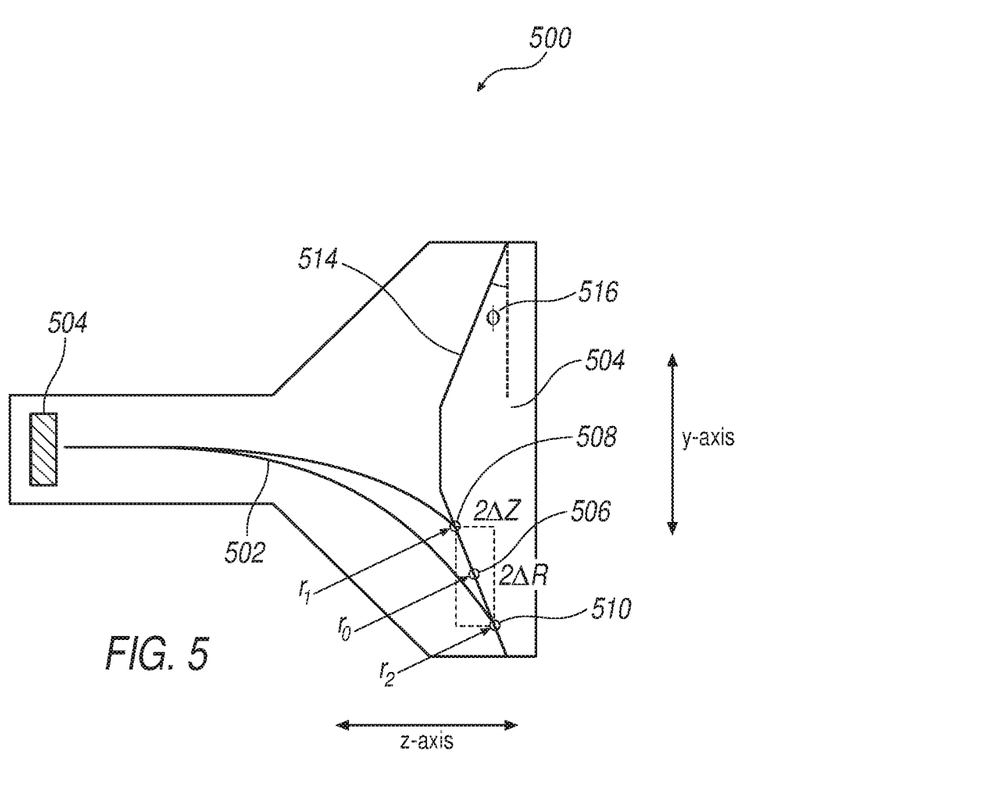
FIG. 5 illustrates an exemplary x-ray tube, used in exemplary implementations of the disclosure.

Referring to FIG. 5, and exemplary x-ray tube 500 is illustrated, which may be implemented according to the disclosure and in reference to the zFFS geometry. X-ray tube 500 includes high energy electrons 502 that are emitted from a cathode 504 and caused to bend by positioning and controlling an electric field toward a focal spot. In a normal or more conventional single focal spot case, electronics hit a target at a single location, such as $f_0$ 506, while in a zFFS arrangement two focal spots $f_1$ or $f_2$ (508 and 510, respectively) are directed toward on an anode, as illustrated in FIG. 5 as anode or anode surface 514. In a zFFS data collection procedure, electrons are directed alternatively to $f_1$ 508 and $f_2$ 510, while x-ray tube 500 is caused to rotate about an isocenter the scanner, such as isocenter 140 above and as illustrated in FIG. 2. $f_1$ 508 and $f_2$ 510 are located away from the virtual focal spot $f_0$ by $\mp \Delta R$ in a radial or y-direction, and $\pm \Delta Z$ in a z-direction. If $f_0$ has a coordinate (−R, 0) in a YZ plane, then $f_1$ 508 and $f_2$ 510 are located at:

$f_1: (-R_1, \Delta Z)$, $f_2: (-R_2, -\Delta Z)$, where:

$R_1 = R + \Delta R$, and $R_2 = R - \Delta R$.

Thus, according to the disclosure, x-ray tube 500 includes external magnetic or other deflection devices (not shown) that serve to deflect high energy electrons 502. In one example, and as known, the trajectory of high energy electrons 502 may be impacted or otherwise affected by including an electrostatic bias device (not shown) proximate cathode 504. High energy electrons 502 emit from cathode 504 and are caused to deflect and emit toward a focal spot. In one example, such bias electrodes may be positioned proximate cathode 504 and to either side thereof (i.e., in and out of the page in FIG. 5), which can cause deflection in of high energy electrons 502 in an x-direction. Thus, in a conventional or single focal spot application, electrons are caused to impinge at location $f_0$ 506 and as is known, rapid deceleration of the high energy electrons, as they impinge on anode 504, cause x-rays to emit from the point of impingement, in this case location $f_0$ 506.

In addition, deflection of the focal spot may be caused to occur via operation of deflection devices, such that deflection occurs along the Z-axis as well. Referred to above as a 'flying focal spot', such also may be referred to as "Z wobble", as well and as another example. As can be seen in FIG. 5, deflection occurs along the illustrated Z-axis, but causing a deflection along the Y-axis as well (also referred to as the radial or "R" dimension). Thus, deflection+/−R causes high energy electrons 502 to impinge at different radial locations upon anode 504. Accordingly, and because of the angle Φ, focal spots $f_1$ 508 and $f_2$ 510 are caused to emit from not only different Z locations on anode 504, but also from different Y locations as well. Thus, referring to FIG. 6A, focal spots 508 and 510 emit, correspondingly, from locations that differ in both Z and Y. And, as can be seen on FIG. 6A, and particularly toward the right side of the Figure, rays emitting respectively from focal spots $f_1$ 508 and $f_2$ 510 pass to individual detectors and, because of the offset of focal spots $f_1$ and $f_2$ in both Y and Z directions, and that rays are drawn to the individual detectors on each (on the right of the figure) a simple geometric layout shows a resulting curve that defines their 'cross-over' pattern, illustrated as item 512.

Figure 6A:
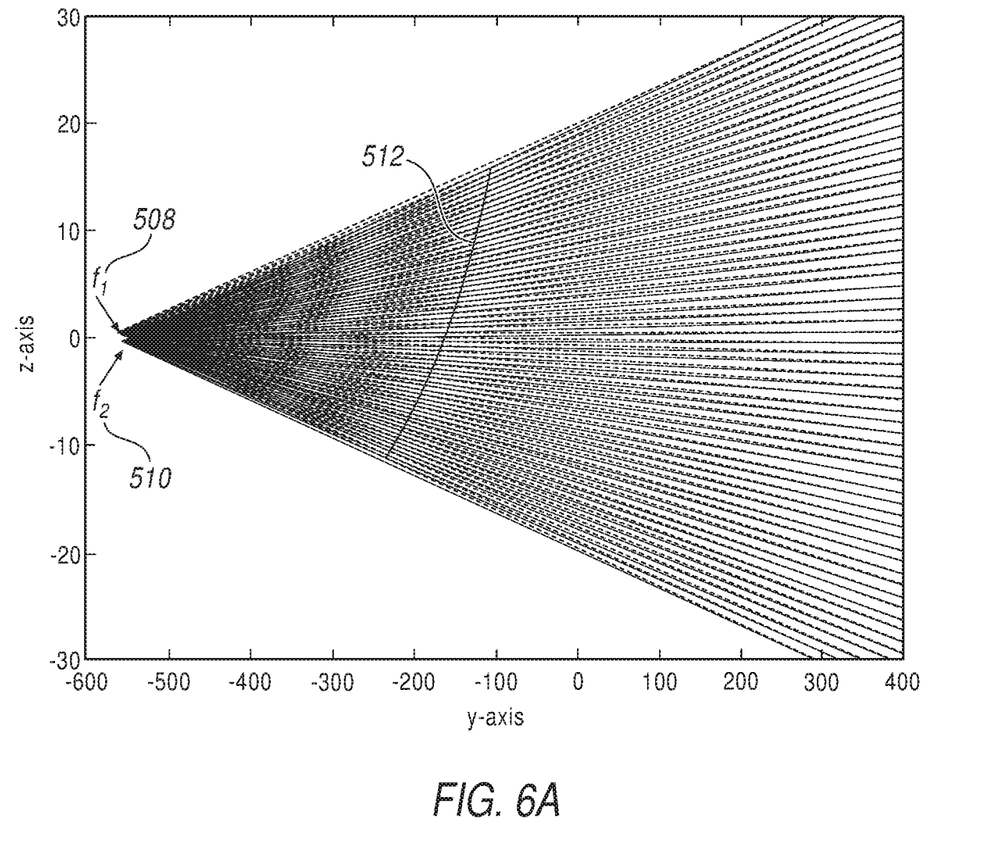
FIG. 6A is an illustration of all rays plotted from focal spots $f_1$ and $f_2$ to one detector pilar.
Figure 6B:
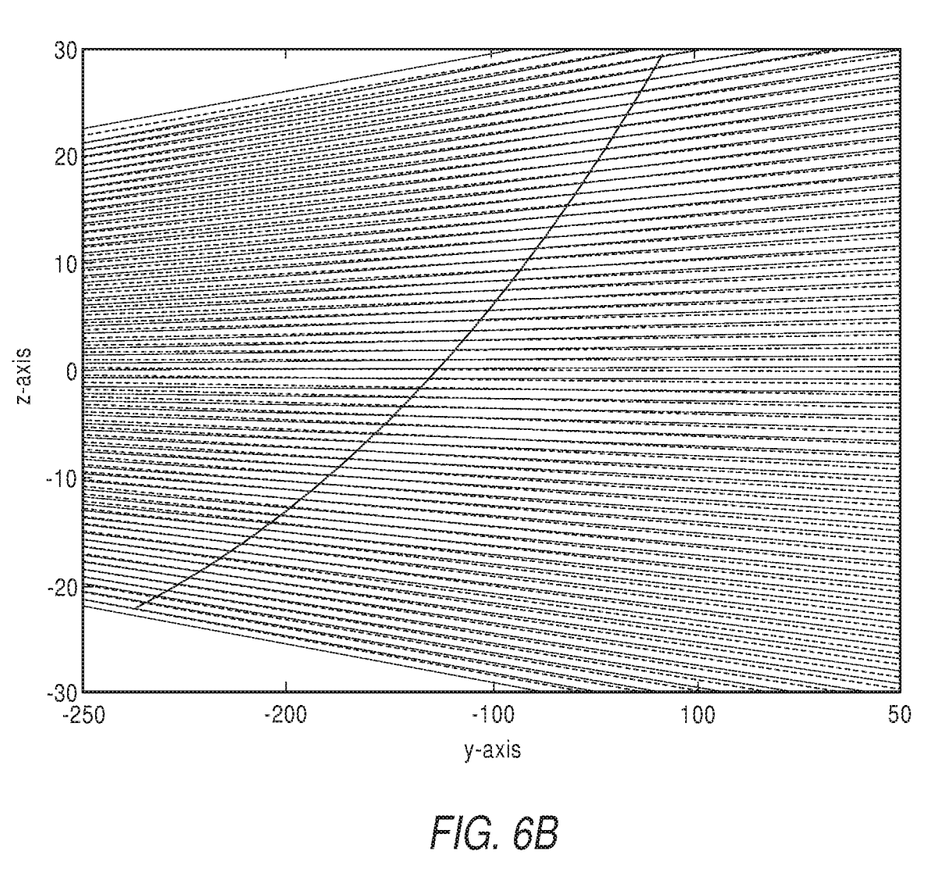
FIG. 6B is an expanded or zoomed view of a portion of FIG. 6A showing a cross-over curve between the sets of rays.

That is. in FIG. 6A, all rays are plotted from focal spots $f_1$ 508 and $f_2$ 510 to one detector pilar, i.e. one channel and all rows, which is evident on the right most side of FIG. 6A. An expanded or zoomed view of a portion of FIG. 6A is shown in FIG. 6B which illustrates the crossover pattern as well and as indicated in the unlabeled curve passing therethrough, which corresponds to item 512 from FIG. 6A. When plotting the geometry of FIGS. 6A and 6B, in one example a "Minfound Scinticare 64 row" scanner is used, which has 64 row detectors each having a height of $T_{det}=1.063$ mm, that is 0.625 mm along the z-axis, thus the z-coverage at the z-axis is 40 mm, and having a cone angle of about ±2°. The focal spot-to-detector distance, $S_{F2D}$, and the iso-to-detector distance, $S_{I2D}$, are 950.42 mm and 392.42 mm respectively, in this example.

For a tube position angle of $f_1$ and a fan angle $\gamma_j$ of rays from f0 to detectors, the $\beta_i$ are usually equally spaced, as well as the $\gamma_j$, and the detector arc has $f_0$ as its circular center. However, for zFFS the fan angle distributions for focal spot $f_1, \gamma_j^{(1)}$, and focal spot $f_2, \gamma_j^{(2)}$, are not equally spaced since neither $f_1$ nor $f_2$ is the circular center of the detector arc.

From FIGS. 6A and 6B, it is clear that:

1) The interleave property of the two set 64 rays is only true for the points beyond the red curve, at which the two set rays cross each other. This is the reason that the current zFFS reconstruction limits its FOV.

2) The interleaved rays are not equally spaced in a z-direction. The interleaved rays are close to equally spaced around the z-axis, and cross at the illustrated and marked curve 512, and the detector plane.

3) For image points close to the focal spots (and within marked curve 512) the interleave property is severely violated.

To create nearly equal spaced rays along the z-axis, and according to the disclosure, control the focal spot position is controlled by grid a potential such that:

$$\Delta Z = \frac{T_{det}}{4} \frac{S_{F2D}}{S_{I2D}}; \qquad \text{Eqn. 1}$$

Because the anode surface 514 has a tilt angle θ 516, typically 7-9%, then $$\Delta R = \Delta Z \cdot \arctan(\phi); \qquad \text{Eqn. 2}$$

Figure 7:
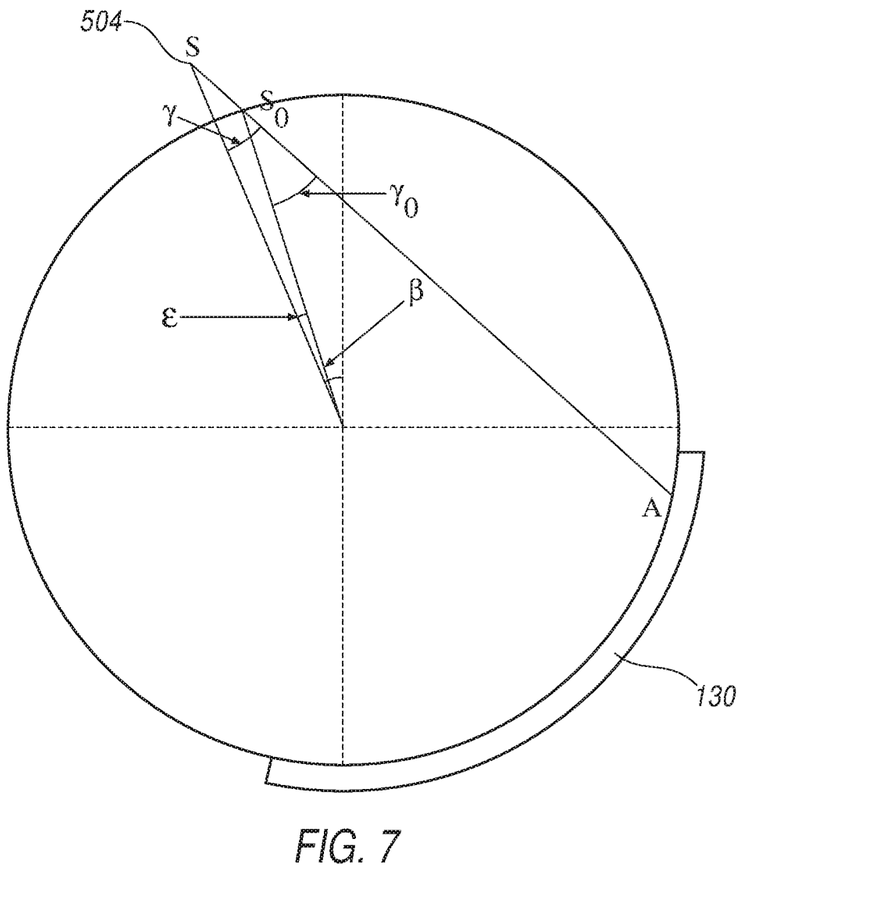
FIG. 7 is an illustration of geometric relationships between an anode and detector assembly, as referenced herein.

Following includes discussion of a re-binning algorithm, according to the disclosure. The disclosed native focal spot-based CB reconstruction includes an analytical type reconstruction algorithm, specifically FDK (Feldman-Davis-Kress) type algorithms. To simplify the problem, circular cone beam (CCB) case is considered. In the disclosed algorithm a fan beam to parallel beam re-binning is performed for each focal spot separately. However, the known azimuthal re-binning formula:

$$\Theta = \beta + \gamma, \qquad \text{Eqn. 3},$$

for an ideal focal spot $f_0$ does not hold for zFFS, since the focal spots in zFFS scanning are not the center of the detector arc. Thus, to perform re-binning the rays are mapped from a deflected source, SA in FIG. 7, for example, to rays emitted from an ideal source circle with associated source position angles and fan angles. FIG. 7 illustrates the relationship of this mapping for focal spot $f_1$. The angles are related with the following formula:

$$\beta = \beta_0 + \epsilon, \text{ and } \gamma = \gamma_0 - \epsilon, \text{ for focal spot } f_1, \quad \text{Eqn. 4a}$$

$$\beta = \beta_0 - \epsilon, \text{ and } \gamma = \gamma_0 + \epsilon, \text{ for focal spot } f_2, \quad \text{Eqn. 4b}$$

The adjustment angle $\epsilon$ is determined by using the known trigonometric relationship, "law of sines", $$\varepsilon = \pi - \gamma - \arcsin\left(\frac{R_1 \cdot \sin(\gamma)}{R}\right), \quad \text{Eqn. 5a}$$

for focal spot $f_1$, and, $$\varepsilon = \gamma - \arcsin\left(\frac{R_2 \cdot \sin(\gamma)}{R}\right), \quad \text{Eqn. 5b}$$

for focal spot, $f2$.

The radial re-binning is the same as for normal or conventional focal spot data re-binning, ensuring to account for an accurate fan angle calculation, $\gamma_j^{(1)}$ and $\gamma_j^{(2)}$, before using $t_1 = R_1 \sin(\gamma_j^{(1)})$ and $R_2 \sin(\gamma_j^{(2)})$ since the fan angles are not equally spaced.

Finally, the target parallel angles and channels of re-binning two data sets should be the same (t, θ), so that the interpolation over the complete parallel data can be performed readily and accurately in the back-projection step.

The disclosed and complete FDK type zFFS reconstruction algorithm for CCB data is disclosed herein in Algorithm 1, which is relevant to the disclosed algorithm and is listed independently in Algorithm 2. The data sorting step 1(c) in Algorithm 2, i.e. row order associated with the two focal spots, may vary for voxels from different regions. For voxels far from the source and at the given projection angle, an interleave order as used in conventional zFFS data will be used in a merge strategy. However, for voxels close to the source, such as within marked curve 512 of FIG. 2, imaging data is processed according to the disclosure.

Algorithm 1 Reconstruction for zFFS CCB Data by Weighted Re-Binning FDK Algorithm:
1: Re-binning the zFFS CCB projection data $p_1(\gamma_1, \upsilon_1, \beta_1)$ and $p_2(\gamma_2, \upsilon_2, \beta_2)$ from fan geometry to parallel geometry with the same target channel/angle (t,θ) for each row υ to produce $p_1(t, \upsilon_1, \theta)$ and $p_2(t, \upsilon_2, \theta)$.
2: Filtering the re-binned projection by kernel h(t).
3: Applying cosine weight to obtain $q_1(t, \upsilon_1, \theta)$ and $q_2(t, \upsilon_2, \theta)$.
4: Performing weighted back-projection, Algorithm 2, to reconstruct the image volume.
Algorithm 2 Weighted Back-Projection for zFFS CCB Data. $q_1(t, \upsilon_1, \theta)$ and $q_2(t, \upsilon_2, \theta)$ are the parallel filtered projection data for two focal spots. Pseud-code of the weighted back-projection for every voxel x is listed below:
For views $\theta_K \in [0,\pi)$, k=1, 2, . . . , K
1) For half turns m=0, 1
   a) For the given voxel x determine the channel position $t_x$
   b) Apply interpolation at channel direction for t for all relevant rows of the two parallel data sets to generate $q_1(t_x, \upsilon_1, \theta_k)$
   c) Build a single z-pilar vector by sorting the two parallel ray sets according to their z-coordinates of the intersection points with vertical line x=x(1), y=x(2).
   d) Perform z-interpolation at z=x(3) to obtain $q(t_x, z, \theta_k)$.
   e) Compute weight accordingly.
2) Normalize weights over half turns.
3) $f(x) = f(x) + \Sigma_{m=0}^{1} w(m,k,x) \cdot q(t_x, z, \theta_k)$ where w(0,k,x)+w(1,k,x)=1.
End For views Further, and according to the disclosure, FIG. 7 includes an illustration of the geometric layout as described above, and the corresponding detector assembly 130 and as illustrated in FIG. 2. Its geometric illustration of the parameters corresponds with the above parameters. The corresponding geometry is described in more detail within Computed Tomography, Principles, Design, Artifacts, and Recent Advances, Second Edition, Jiang Hsieh, Wiley Interscience, Copyright 2009, on page 96 and as illustrated and described with respect to FIG. 3.37 therein, which is incorporated by reference.

Figure 8:
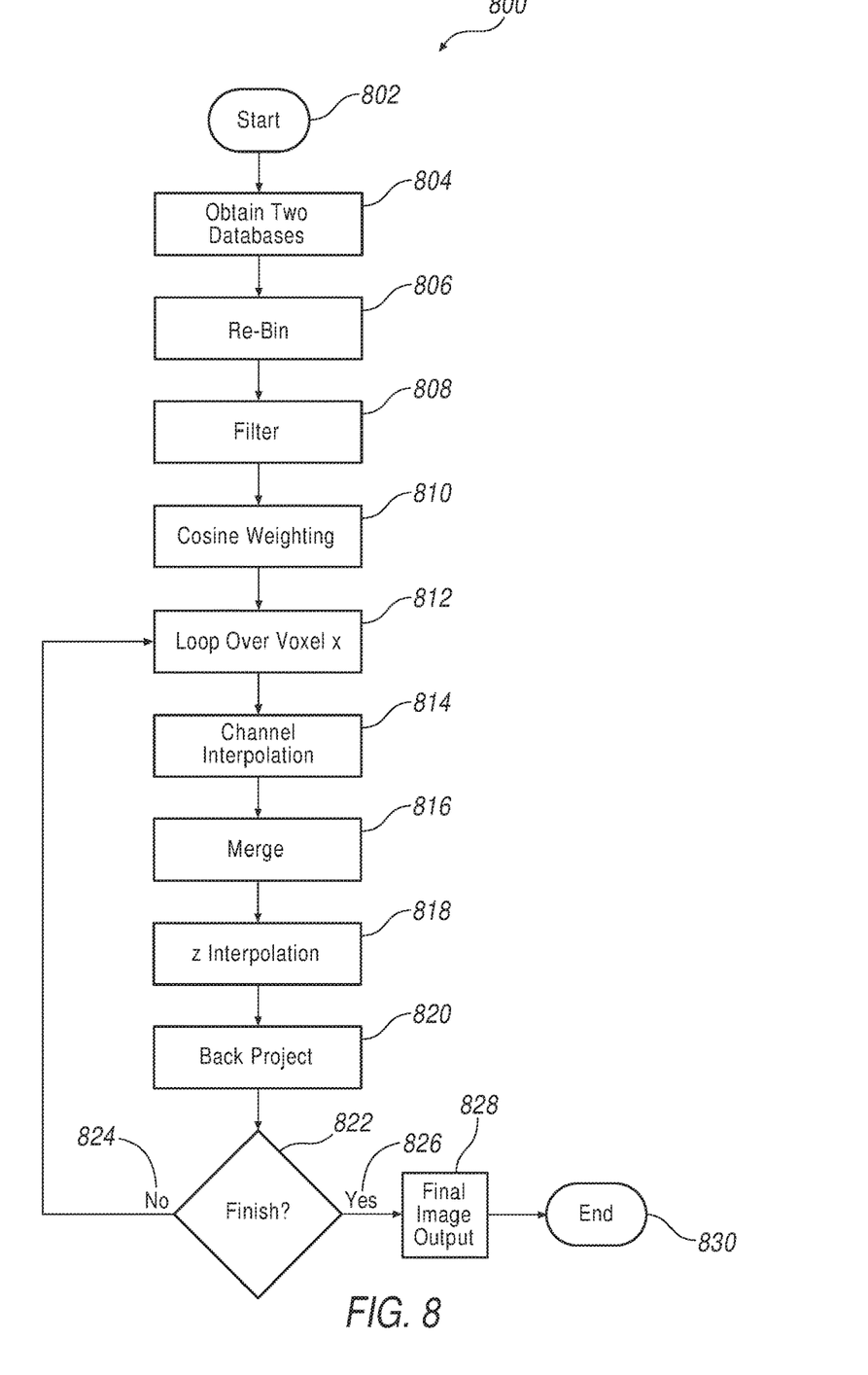
FIG. 8 is an overview of the disclosed reconstruction method of z-flying focal spot scans.

FIG. 8 is an overview of the disclosed method of z-flying focal spot reconstruction and according to the algorithms 1 and 2 disclosed above. Referring to FIG. 8, method or process 800 begins at step 802, and at step 804 two raw datasets for two focal spots are obtained or acquired in fan geometry. In one example the acquired data is helical data and in another example the acquired data is axial data. At step 806 the acquired fan geometry data is re-binned to parallel geometry for each row. At step 808 the re-binned projection data is filtered by, in one example, ram filtering for each row. A cosine weighting is applied for each row at step 810. At step 812 a loop over each voxel x begins, for the projection angle theta over 0 to 2π. At step 814, for the given pixel and angle, interpolation is performed in the channel direction for each data set to produce two vectors in the z-direction. At step 816 the two vectors are merged and sorted. At step 818, z-interpolation is computed for the given pixel, and at step 820 the interpolated data is back-projected with weight, and the value is accumulated to the image volume. At step 822 the data sets are assessed, and if all x and theta have not been processed 824, then control returns to step 812. If so 826, then a final image is output at step 828 and the process ends at step 830.

Thus, according to the disclosure, a computed tomography (CT) system includes a rotatable gantry having an opening to receive an object to be scanned, an x-ray tube having an anode, the x-ray tube positioned on the rotatable gantry to generate x-rays from a first focal spot at a first z-location, and from a second focal spot at a second z-location, a pixelated detector positioned on the rotatable gantry to receive the x-rays from the first z-location and from the second z-location, and a computer. The computer is programmed to acquire a first dataset in a fan geometry at a first z-location, acquire a second dataset in the fan geometry at a second z-location, and reconstruct an image based on the first dataset and the second dataset, wherein the reconstruction is performed without combining the first dataset and the second dataset into one dataset with a single geometry from which the image reconstruction is performed.

Also according to the disclosure, a method of computed tomography (CT) imaging includes acquiring a first dataset in a fan geometry at a first z-location of an x-ray tube anode, acquiring a second dataset in the fan geometry at a second z-location of the x-ray tube anode, and reconstructing an image based on the first dataset and the second dataset. The reconstruction is performed without combining the first dataset and the second dataset into one dataset with a single geometry from which the image reconstruction is performed.

Disclosed is a new reconstruction algorithm for zFFS scans. The disclosed algorithm uses the native two focal spots to perform the image reconstruction instead of combining the two sets of data. By doing so the native geometry of each of the rays is used, thus the object to be reconstructed can include voxels beyond the limited FOV. The algorithm has been validated with offset zFFS scan of a physical head phantom. The image reconstructed by Algorithm 1 does not show artifacts due to data misplacement for large FOV while the data combining method does, illustrating that the disclosed algorithm has overcome the FOV limitation for zFFS scans.

When introducing elements of various embodiments of the disclosed materials, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection or imaging techniques.

While the disclosed materials have been described in detail in connection with only a limited number of embodiments, it should be readily understood that the embodiments are not limited to such disclosed embodiments. Rather, that disclosed can be modified to incorporate any number of variations, alterations, substitutions or equivalent arrangements not heretofore described, but which are commensurate with the spirit and scope of the disclosed materials. Additionally, while various embodiments have been described, it is to be understood that disclosed aspects may include only some of the described embodiments. Accordingly, that disclosed is not to be seen as limited by the foregoing description, but is only limited by the scope of the appended claims.

What is claimed is:

1. A computed tomography (CT) system, comprising:
   a rotatable gantry having an opening to receive an object to be scanned;
   an x-ray tube having an anode, the x-ray tube positioned on the rotatable gantry to generate x-rays from a first focal spot at a first z-location, and from a second focal spot at a second z-location;
   a pixelated detector positioned on the rotatable gantry to receive the x-rays from the first z-location and from the second z-location; and
   a computer programmed to:
      acquire a first dataset in a fan geometry at a first z-location;
      acquire a second dataset in the fan geometry at a second z-location; and
      reconstruct an image based on the first dataset and the second dataset, wherein the reconstruction is performed without combining the first dataset and the second dataset into one dataset with a single geometry from which the image reconstruction is performed.

2. The CT system of claim 1, wherein the computer is further programmed to interpolate in a channel direction for each of the first and second datasets to produce two vectors of projection data in a z-direction.

3. The CT system of claim 2, wherein the computer is further programmed to merge the two vectors.

4. The CT system of claim 3, wherein the computer is further programmed to interpolate in the z-direction to compute interpolated projection data for a given pixel.

5. The CT system of claim 4, wherein the computer is further programmed to process the first and second datasets by looping over each voxel x in the image and over the projection data of an angle theta from 0 to $2\pi$.

6. The CT system of claim 4, wherein the computer is further programmed to back-project the interpolated projection data with a weight, and accumulate a value in an image volume.

7. The CT system of claim 1, wherein the computer is further programmed to re-bin the first dataset and the second dataset to a parallel geometry.

8. The CT system of claim 7, wherein the computer is further programmed to filter the re-binned projection data by ram filtering for each row.

9. The CT system of claim 8, wherein the computer is further programmed to apply a cosine weight to each row.

10. The CT system of claim 1, wherein the first dataset and the second dataset are acquired as one of helical data and axial data.

11. A method of computed tomography (CT) imaging, comprising:
    acquiring a first dataset in a fan geometry at a first z-location of an x-ray tube anode;
    acquiring a second dataset in the fan geometry at a second z-location of the x-ray tube anode; and
    reconstructing an image based on the first dataset and the second dataset;
    wherein the reconstruction is performed without combining the first dataset and the second dataset into one dataset with a single geometry from which the image reconstruction is performed.

12. The method of claim 11, wherein the first and second datasets are acquired using:
    a rotatable gantry having an opening to receive an object to be scanned;
    an x-ray tube having an anode, the x-ray tube positioned on the rotatable gantry to generate x-rays from a first focal spot at a first z-location, and from a second focal spot at a second z-location; and
    a pixelated detector positioned on the rotatable gantry to receive the x-rays from the first z-location and from the second z-location.

13. The method of claim 12, further comprising interpolating in a channel direction for each of the first and second datasets to produce two vectors of projection data in a z-direction.

14. The method of claim 13, further comprising merging the two vectors.

15. The method of claim 14, wherein the step of interpolating includes interpolating in the z-direction to compute interpolated projection data for a given pixel.

16. The method of claim 15, further comprising processing the first and second datasets by looping over each voxel x in the image and over the projection data of an angle theta from 0 to $2\pi$.

17. The method of claim 15, further comprising back-projecting the interpolated projection data with a weight, and accumulate a value in an image volume.

18. The method of claim 11, further comprising re-binning the first dataset and the second dataset to a parallel geometry.

19. The method of claim 18, further comprising filtering the re-binned projection data by ram filtering for each row.

20. The method of claim 19, further comprising applying a cosine weight to each row.

* * * * *